United States Patent
Brown et al.

(10) Patent No.: US 10,466,220 B1
(45) Date of Patent: Nov. 5, 2019

(54) ALERTING FOR INSTRUMENTS THAT TRANSFER PHYSICAL SAMPLES

(71) Applicant: Pace Analytical Services, LLC, Minneapolis, MN (US)

(72) Inventors: Joshua R. Brown, Shelbyville, TN (US); Kathleen A. Zenisek, Lebanon, TN (US); Peter A. Schulert, Mount Juliet, TN (US); Forest W. Darling, Mount Juliet, TN (US)

(73) Assignee: Pace Analytical Services, LLC, Minneapolis, MN (US)

( * ) Notice: Subject to any disclaimer, the term of this patent is extended or adjusted under 35 U.S.C. 154(b) by 0 days.

(21) Appl. No.: 16/137,581

(22) Filed: Sep. 21, 2018

(51) Int. Cl.
*G01N 33/00* (2006.01)
*G08B 5/22* (2006.01)
*G08B 3/10* (2006.01)
*G08B 21/18* (2006.01)

(52) U.S. Cl.
CPC ....... *G01N 33/0065* (2013.01); *G08B 3/1016* (2013.01); *G08B 5/223* (2013.01); *G08B 21/182* (2013.01)

(58) Field of Classification Search
CPC ........... G01N 33/0065; G01N 33/0067; G01N 33/007; G01N 33/0027; G08B 3/1016; G08B 5/223; G08B 21/182
USPC ........................................................ 340/540
See application file for complete search history.

(56) References Cited

U.S. PATENT DOCUMENTS

| | | | |
|---|---|---|---|
| 5,097,469 A | 3/1992 | Douglas | |
| 5,097,470 A | 3/1992 | Gihl | |
| 5,210,757 A | 5/1993 | Barlow et al. | |
| 5,534,851 A | 7/1996 | Russek | |
| 5,610,835 A * | 3/1997 | Dominguez | G01N 30/62 436/161 |
| 6,108,571 A | 8/2000 | Minoz et al. | |
| 6,442,639 B1 | 8/2002 | McElhattan et al. | |
| 7,026,926 B1 | 4/2006 | Walker, III | |
| 7,536,594 B2 | 5/2009 | Schaff et al. | |
| 7,928,850 B2 * | 4/2011 | Hayter | A61B 5/0002 340/573.1 |
| 8,843,221 B2 | 9/2014 | Wang et al. | |
| 9,798,601 B2 | 10/2017 | Piekarski | |
| 9,964,937 B2 | 5/2018 | Koh | |
| 2002/0085499 A1 | 7/2002 | Toyoyama et al. | |
| 2007/0050687 A1 | 3/2007 | Disser et al. | |

(Continued)

*Primary Examiner* — Emily C Terrell
(74) *Attorney, Agent, or Firm* — Fredrikson & Byron P.A.

(57) ABSTRACT

Techniques for alerting for instruments that transfer physical samples are disclosed. An alarm module, placed within a communication pathway of a first chemical processor and a second chemical processor, includes a timer configured to count time elapsed since receiving, from the first chemical processor, a transfer-ready signal indicating that 1) the first chemical processor received a receive-ready signal from the second chemical processor; ii) the first chemical processor has completed processing a chemical analyte; and iii) the first chemical processor is ready to physically transfer the chemical analyte to the second chemical processor. Upon receiving the transfer-ready signal from the first chemical processor, the timer is restarted. An alarm triggers when the elapsed time counted by the timer exceeds a specified threshold. The alarm is audible or visual. Upon the triggering of an alarm, an alert notification (e.g., an email, a text message, etc.) is transmitted.

26 Claims, 9 Drawing Sheets

(56) References Cited

U.S. PATENT DOCUMENTS

| | | |
|---|---|---|
| 2007/0078629 A1 | 4/2007 | Gollhardt et al. |
| 2010/0127860 A1* | 5/2010 | Ganguly ............ G01N 30/8693 340/540 |
| 2014/0019092 A1 | 1/2014 | Phelps et al. |
| 2015/0325097 A1* | 11/2015 | Misra .................... G08B 21/18 340/540 |
| 2016/0261482 A1 | 9/2016 | Mixer et al. |
| 2018/0144600 A1 | 5/2018 | Grubis et al. |

* cited by examiner

ALERTING FOR INSTRUMENTS THAT TRANSFER PHYSICAL SAMPLES

TECHNICAL FIELD

The present disclosure relates generally to chemical instruments, and specifically to alerting for chemical instruments that transfer physical samples between one another.

BACKGROUND

Like other devices, chemical instruments that transfer physical samples between each other are susceptible to hardware and software failures. However, in addition to hardware and software failures, chemical instruments that transfer physical samples between each other may also cause a chemical process to fail if a physical sample is not transferred or not properly transferred.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments or examples discussed in the present document.

DETAILED DESCRIPTION

The present disclosure describes methods, systems, and computer program products that individually enable alerting for chemical instruments that transfer physical samples between one another. In the following detailed description, for purposes of explanation, numerous specific details are set forth in order to provide a thorough understanding of the various aspects of the presently disclosed subject matter. However, it will be evident to those skilled in the art, after reading and understanding the present subject matter, that the presently disclosed subject matter may be practiced without these specific details. In other instances, well-known methods, procedures, and components have not been described in detail so as not to obscure the presently disclosed subject matter.

Many chemical labs have chemical instruments that transfer physical samples (e.g., solids, liquids, gases, or some combination thereof) between each other. For example, an auto-sampler uses its robotic arm to pick up a sample (a vial of liquid) and then transfers the sample to another device; a gas chromatograph receives a gas analyte (e.g., a mixture of gases with a carrier gas) from another device and analyzes the gas sample to determine its chemical compounds, etc.

Unfortunately, most chemical instruments today do not have a mechanism to alert or notify in the event of an unsuccessful transfer of a physical sample; when an unsuccessful transfer of a physical sample occurs with such chemical instruments, the chemical instrument may simply stay in an idle state until a human intervenes. If the idled chemical instrument is part of a sequential chemical process involving other chemical instruments, the idled chemical instrument may cause the entire chemical process to halt until a human intervenes. Some chemical instruments have proprietary alerting mechanisms provided by their respective manufacturers. However, most chemical laboratories use instruments from a number of different manufacturers; to determine accurately the status of all of the chemical instruments used in a laboratory, a user might need to access a dozen or more proprietary software platforms.

Figure 1:
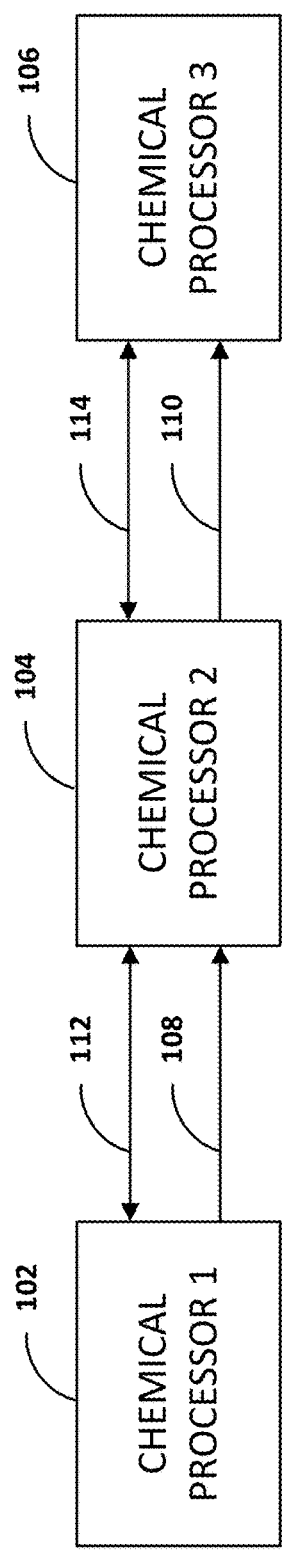
FIG. 1 is a system diagram illustrating a system including a sequence of chemical instruments that transfer physical samples, according to an example embodiment.

FIG. 1 illustrates a system 100 that includes a sequence of chemical instruments that transfer physical samples, according to an example embodiment. For example, an auto-sampler uses its robotic arm to pick up sample (a vial of liquid), and then transfers the sample to a purge and trap device. The purge and trap device "bubbles" the sample with an inert gas (e.g., helium), and transfers the resulting gas to a gas chromatograph. The gas chromatograph then analyzes the gas to determine its chemical compounds.

For this chemical process 100 to work properly, the chemical instruments must coordinate with each other to make sure that 1) a transferring instrument is ready to transfer a physical sample to a receiving instrument and 2) a receiving instrument is ready to receive the physical sample from the transferring instrument. To enable such coordination, many chemical instruments communicate using standardized protocols over standardized interfaces 112, 114. For example, when chemical processor 2 104 is ready to receive a physical sample from the chemical processor 1 102, the chemical processor 2 104 may transmit a receive-ready signal to chemical processor 1 102 via their shared standardized interface 112. Likewise, when the chemical processor 1 102 is ready to transmit a physical sample to the chemical processor 2 104, the chemical processor 1 102 may transmit a transmit-ready signal to the chemical processor 2 104 via their shared standardized interface 112. A similar exchange of receive-ready and transmit-ready signals occurs between chemical processor 2 104 and chemical processor 3 106 via their shared standardized interface 114.

Unfortunately, despite the successful exchange of receive-ready and transmit-ready signals between two instruments, physical samples are sometimes not transferred properly, or not transferred at all. Unsuccessful transfers of physical samples may be caused by an almost infinite variety of causes (e.g., power failure, mechanical failure of a moving part, an earthquake causing a sample to spill, etc.).

Figure 2:
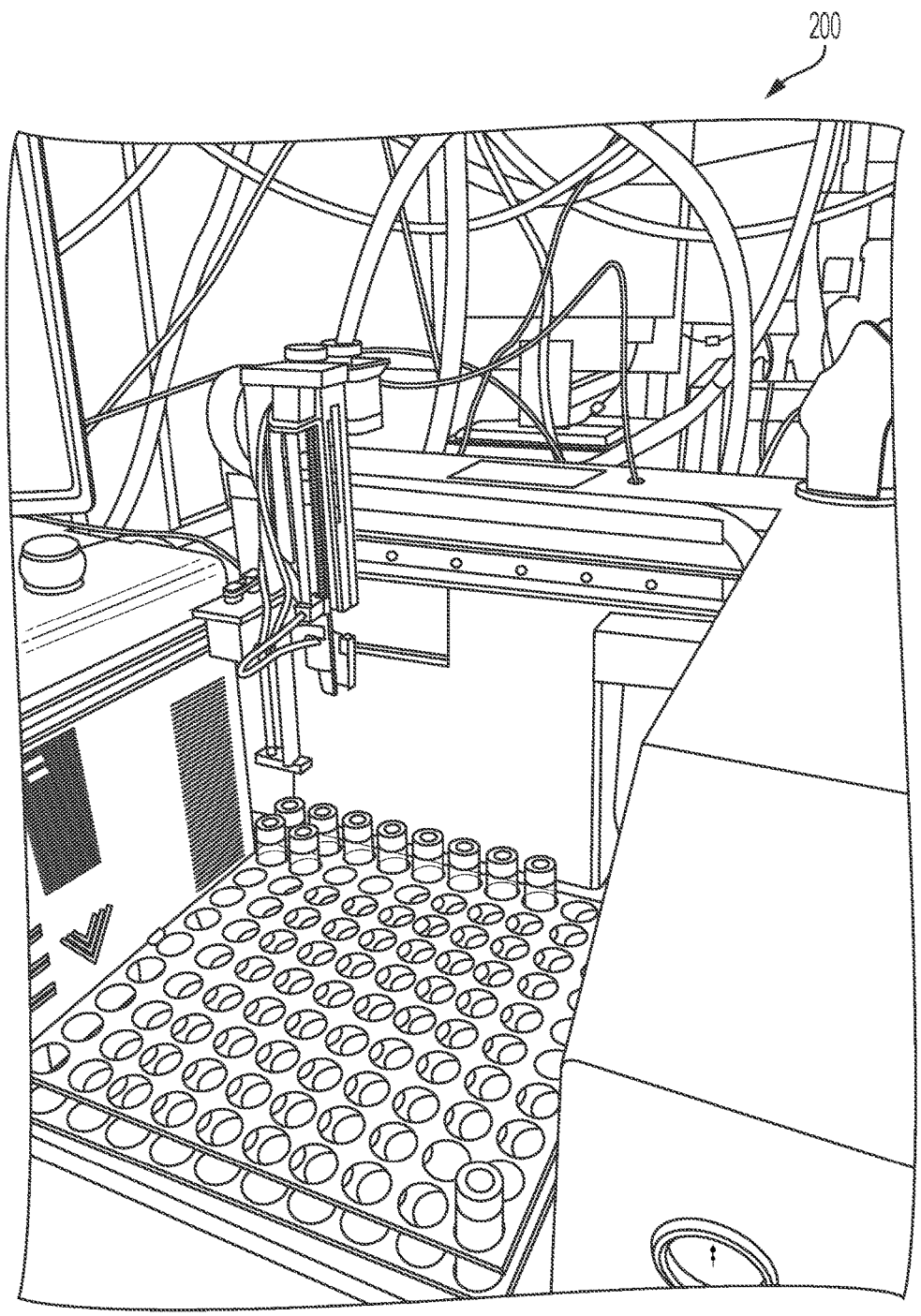
FIG. 2 illustrates an auto sampler that picks up a chemical vial from a rack and transfers the chemical vial to another chemical instrument, according to an example embodiment.

FIG. 2 illustrates an auto sampler that picks up a chemical vial from a rack and transfers the chemical vial to another chemical instrument, according to an example embodiment.

The auto-sampler has a robotic arm that picks up a vial from the rack and transfers the vial to another chemical instrument.

Figure 3:
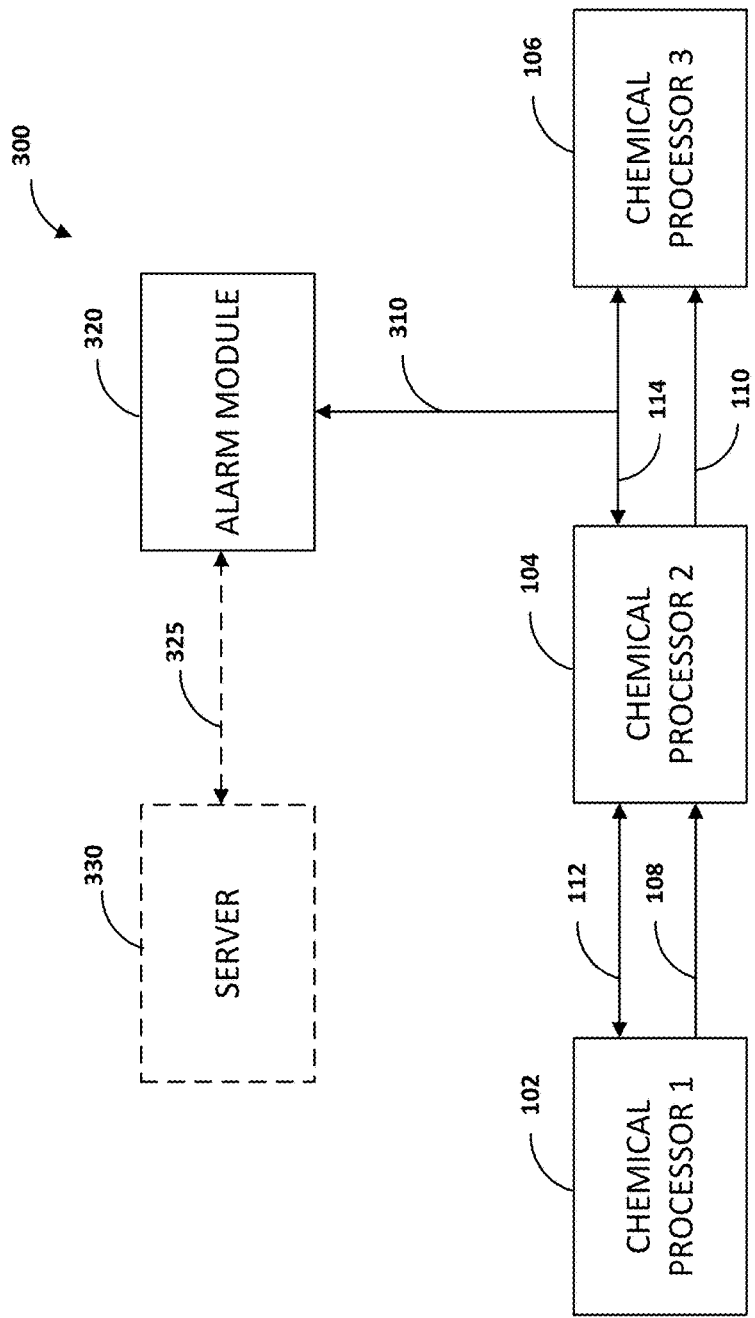
FIG. 3 is a system diagram illustrating an alerting system connected to a sequence of chemical instruments that transfer physical samples, according to an example embodiment.

FIG. 3 illustrates a system 300 that includes an alerting system connected to a sequence of chemical instruments that transfer physical samples, according to an example embodiment. The chemical instruments 102, 104, 106 are the same as those in FIG. 1; however, an alarm module 320 is now connected inline of the standardized interface 114 between chemical processor 2 104 and chemical processor 3 106.

The alarm module 320 includes a processor, a memory, and a timer. The alarm module 320 allows transfer-ready and receive-ready signals to travel between chemical processor 2 104 and chemical processor 3 106 via standardized interface 114; however, the alarm module 320 also monitors the signals that are transmitted via standardized interface 114. The transfer-ready and receive-ready signals may constitute many different types of communication signals indicative of the transfer-ready or receive ready messages. For instance, a transfer-ready signal may be in the form of a start signal from chemical processor 2. Chemical processor 2 is ready to transfer a physical sample if it transmits a start signal. Similarly, chemical processor 3 may transmit a signal indicating that its previous process is complete, indicating that chemical processor 3 is ready to receive the next physical transfer of an analyte.

The timer in the alarm module 320 is configured to count the amount of time that has elapsed since the alarm module 320 last received a transfer-ready signal. The alarm module 320 monitors for a transfer-ready signal transmitted from chemical processor 2 104 to chemical processor 3 106; this transfer-ready signal indicates that i) chemical processor 2 104 received a receive-ready signal from chemical processor 3 106 over the standardized interface 114, ii) chemical processor 2 104 has completed its processing of the physical sample, and iii) chemical processor 2 104 is ready to transfer the physical sample to chemical processor 3 106. When the alarm module 320 detects the transfer-ready signal from chemical processor 2 104, the alarm module 320 restarts its timer.

If the elapsed time counted by the timer exceeds a specified threshold (which is stored in memory), the alarm module 320 initiates an alarm, which indicates that either chemical processor 2 104 or chemical processor 3 106 is not operating properly. Proper operation of chemical processor 2 104 depends upon proper operation of chemical processor 1 102; thus, if the alarm indicates that chemical processor 2 104 is not operating properly, the actual culprit that is not operating properly may be chemical processor 1 102. In an embodiment, the specified threshold is set at a time within the range of between 5 and 45 minutes. In an embodiment, the specified threshold is set for 30 minutes.

In an embodiment, the alarm module 320 is connected inline within the standardized interface 114 between chemical processor 2 104 and chemical processor 3 106; in such an embodiment, communication line 310 is standardized interface 114. For example, alarm module 320 may be connected inline within a DB9 connection 114 between chemical processor 2 104 and chemical processor 3 106. In another embodiment, a signal monitoring device is connected inline within the standardized interface 114 between chemical processor 2 104 and chemical processor 3 106, and the signal monitoring device is then connected to alarm module 320 via communication line 310. For example, a signal monitoring device may be connected inline within a DB9 connection 114 between chemical processor 2 104 and chemical processor 3 106, and the signal monitoring device may be connected 310 to alarm module 320 via a wired connection (e.g., a 3.5 mm audio cable, an RJ-45 connection, etc.) or via a wireless connection (e.g., Bluetooth, ZigBee, 802.11x, etc.).

In an optional embodiment, alarm module 320 communicates 325 with a server 330. The server 330 may enable alarm module 320 to send alert notifications to remote devices via one or more modalities (e.g., email, text messaging, phone calls, etc.). The server 330 may also enable logging of events (e.g., detection of transfer-ready signals, detection of receive-ready signals, alerts, notifications, etc.), for example into a database. The server 330 may also allow remote devices to see the status of instruments monitored by one or more alarm modules 320, and may also allow remote devices to control one or more alarm modules 320.

The communication connection 325 between alarm module 320 and server 330 may be a wired connection (e.g., a CAT5/6 connection, a fiber-optic connection, etc.) or via a wireless connection (e.g., 802.11x, etc.). In an embodiment, alarm module 320 and server 330 are integrated into one device.

Figure 4:
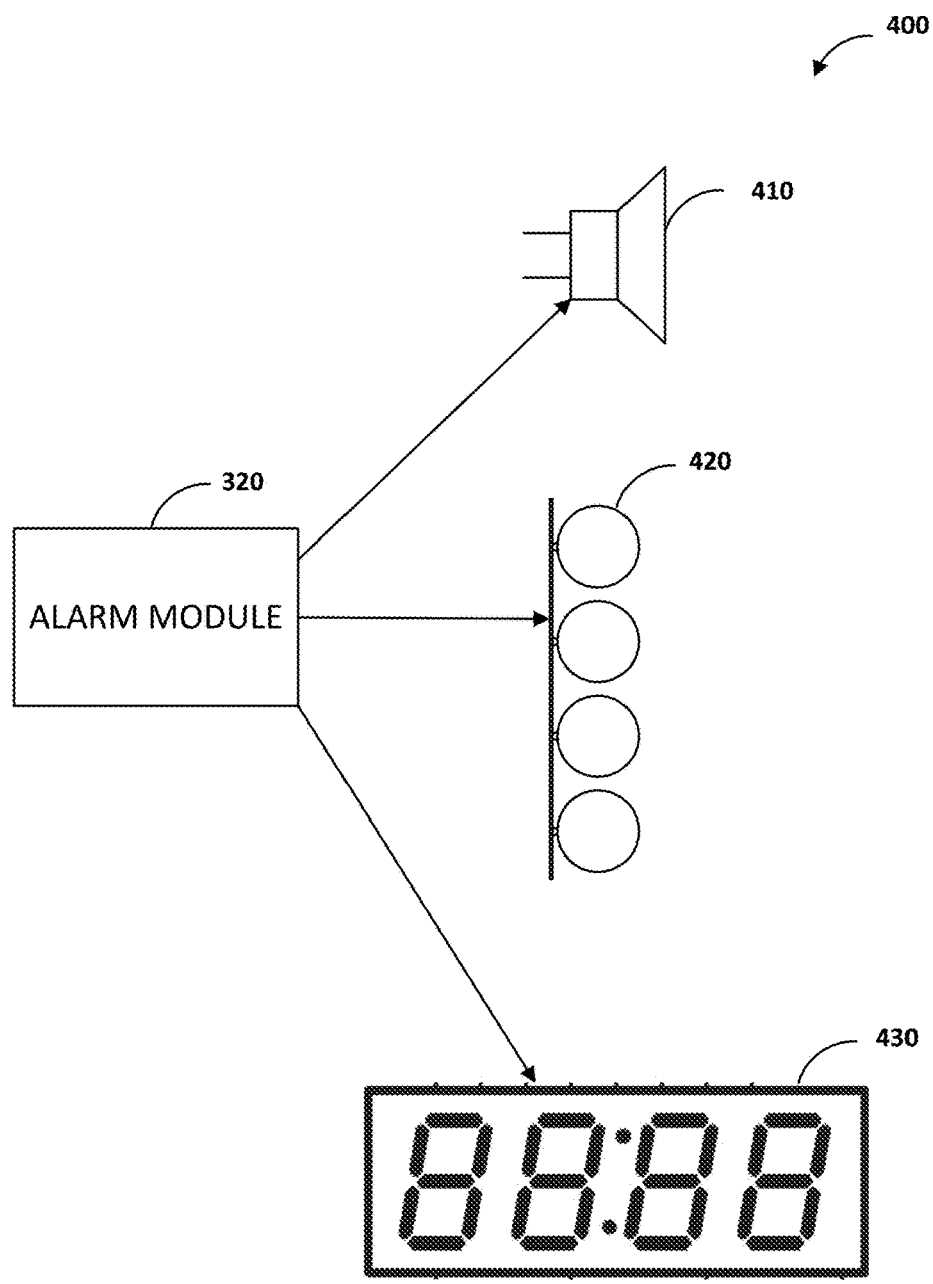
FIG. 4 is a diagram of an alarm module connected to various alerting devices, according to an example embodiment.

FIG. 4 is a diagram of an alarm module connected to various alerting devices, according to an example embodiment. Alarm module 320 may be connected to one or more of a speaker 410, lights 420, and alphanumeric display 430. When alarm module 320 initiates an alarm, the alarm may activate one or more of these devices. For example, regular alarms may activate the lights 420, whereas emergency alarms may activate the speaker 410 and lights 420. The alphanumeric display 430 may display the elapsed time since the alarm module detected the most recent transfer-ready signal. One or more of speaker 410, lights 420, and alphanumeric display 430 may be integrated into alarm module 320.

Figure 5A:
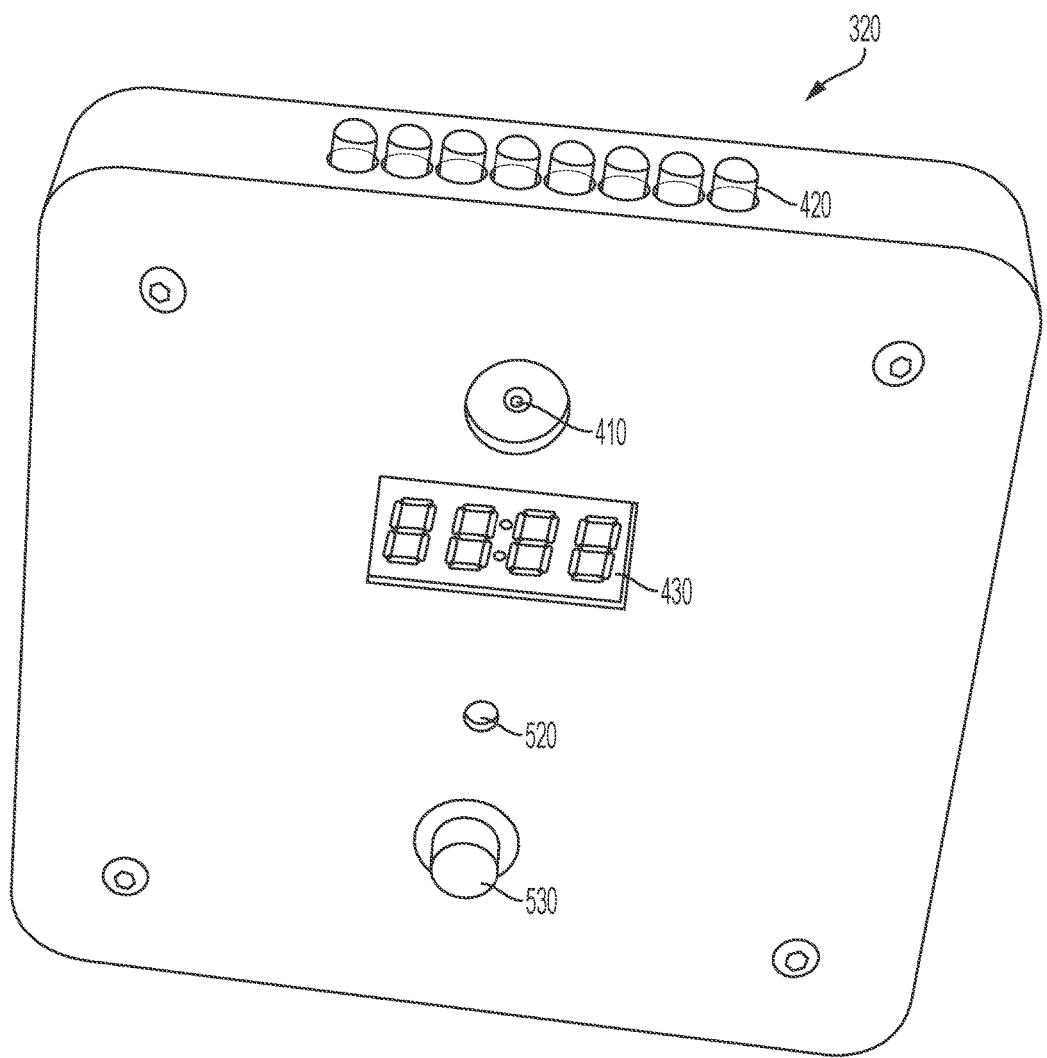
FIG. 5A is an illustration of an alarm module, according to an example embodiment.
Figure 5B:
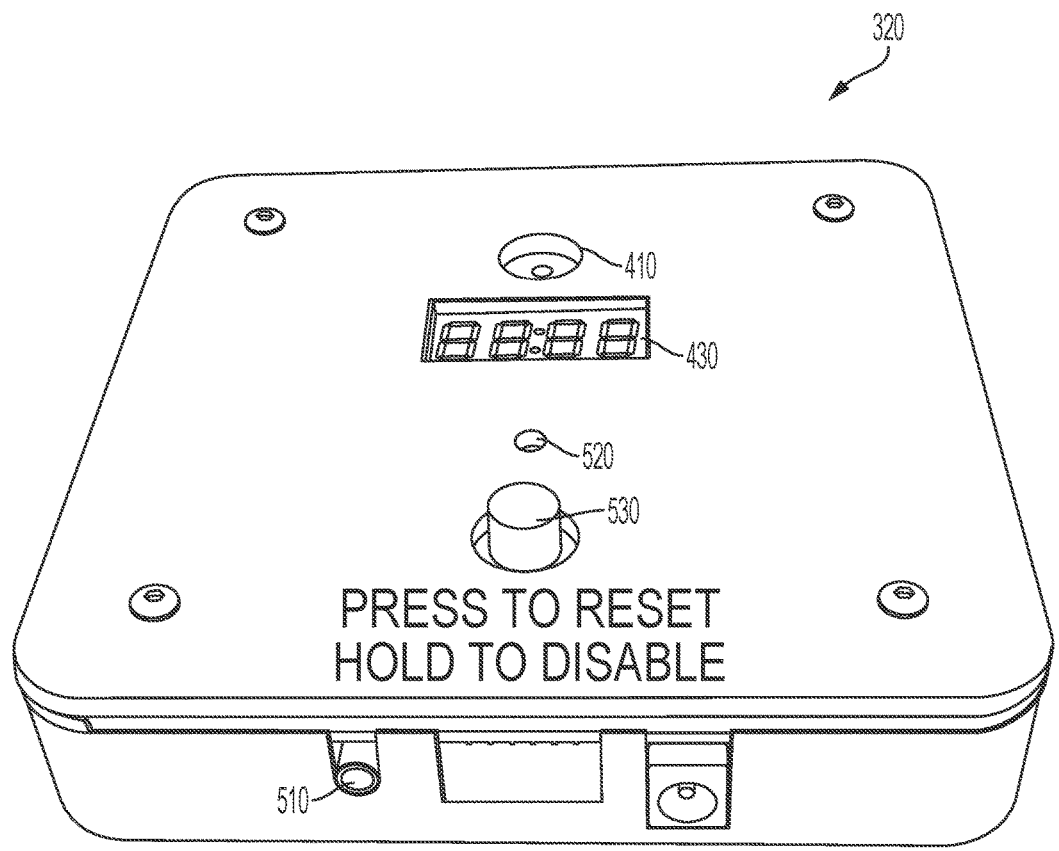
FIG. 5B is an illustration of the alarm module of FIG. 5A shown from a different perspective.

FIGS. 5A and 5B are illustrations of an alarm module 320, according to an example embodiment. Alarm module 320 has integrated lights 420, an audio speaker 410, and an alphanumeric display 430. The audio port 510 allows the alarm module 320 to connect to a signal monitoring device, which is connected inline within a standardized interface between two instruments (see link 310 in FIG. 3). Of course, many types of data interfaces can be employed to achieve the same purpose of data transfer into the alarm module 320. The microcontroller reset button 520 allows a user to manually reset the microcontroller of the alarm module 320. The user interface button 530, when pressed, resets the timer of alarm module 320. If the user interface button 530 is pressed and held for more than a specified period of time (e.g., six seconds), the timer of the alarm module 320 is disabled.

Figure 6:
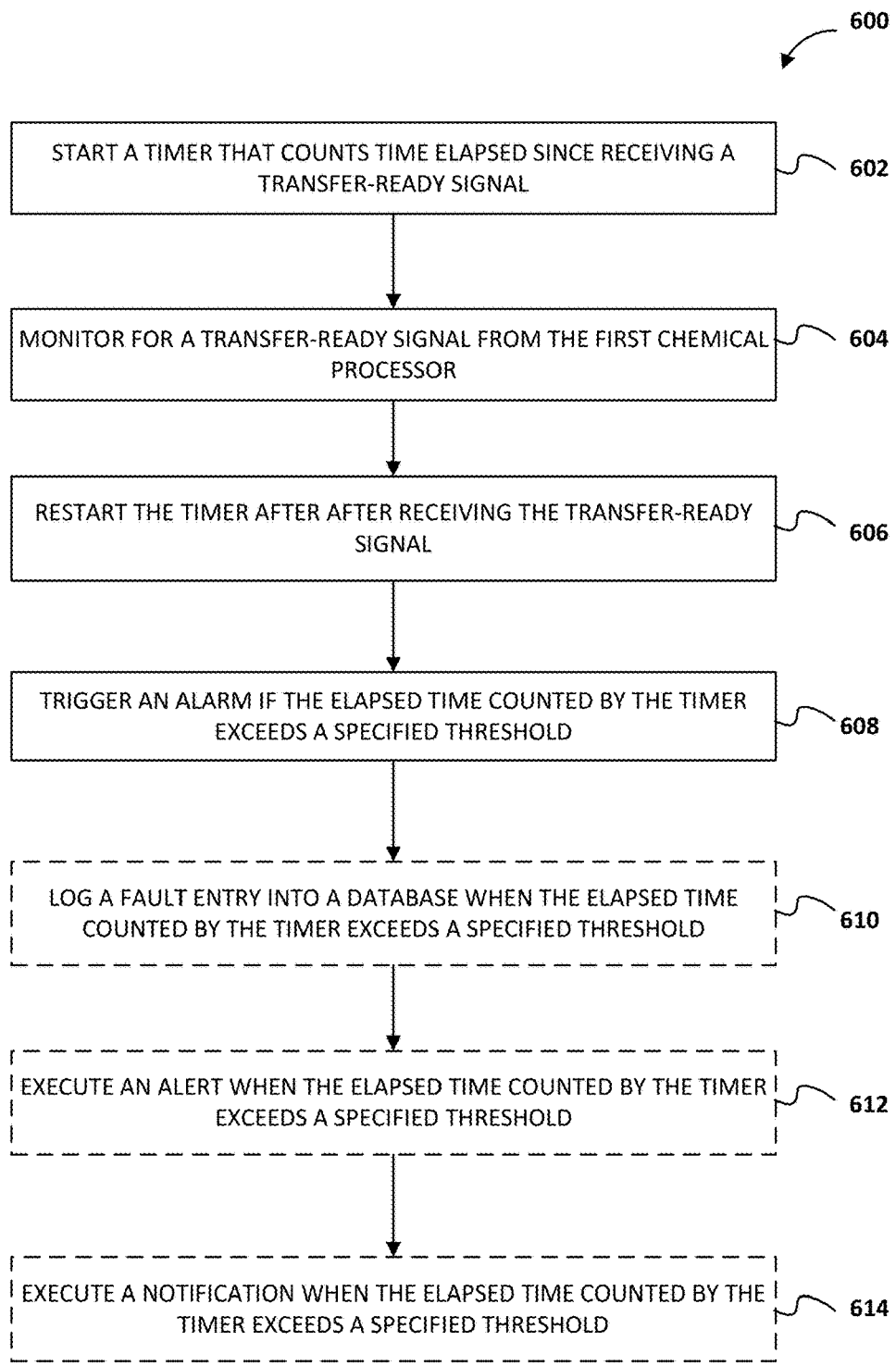
FIG. 6 is a flow diagram of a process performed by an alarm module, according to an example embodiment.

FIG. 6 is a flow diagram of a process 600 performed by an alarm module 320, according to an example embodiment. A timer that counts time elapsed since receiving a transfer-ready signal is started (operation 602).

A transfer-ready signal from the first chemical processor is monitored (operation 604).

After receiving the transfer-ready signal, the timer is restarted (operation 606).

If the elapsed time counted by the timer exceeds a specified threshold, an alarm is triggered (operation 608).

Optionally, when the elapsed time counted by the timer exceeds a specified threshold, a fault entry is logged into a database (operation 610).

Optionally, when the elapsed time counted by the timer exceeds a specified threshold, an alert is executed (operation 612).

Optionally, when the elapsed time counted by the timer exceeds a specified threshold, a notification is executed (operation 614).

Figure 7:
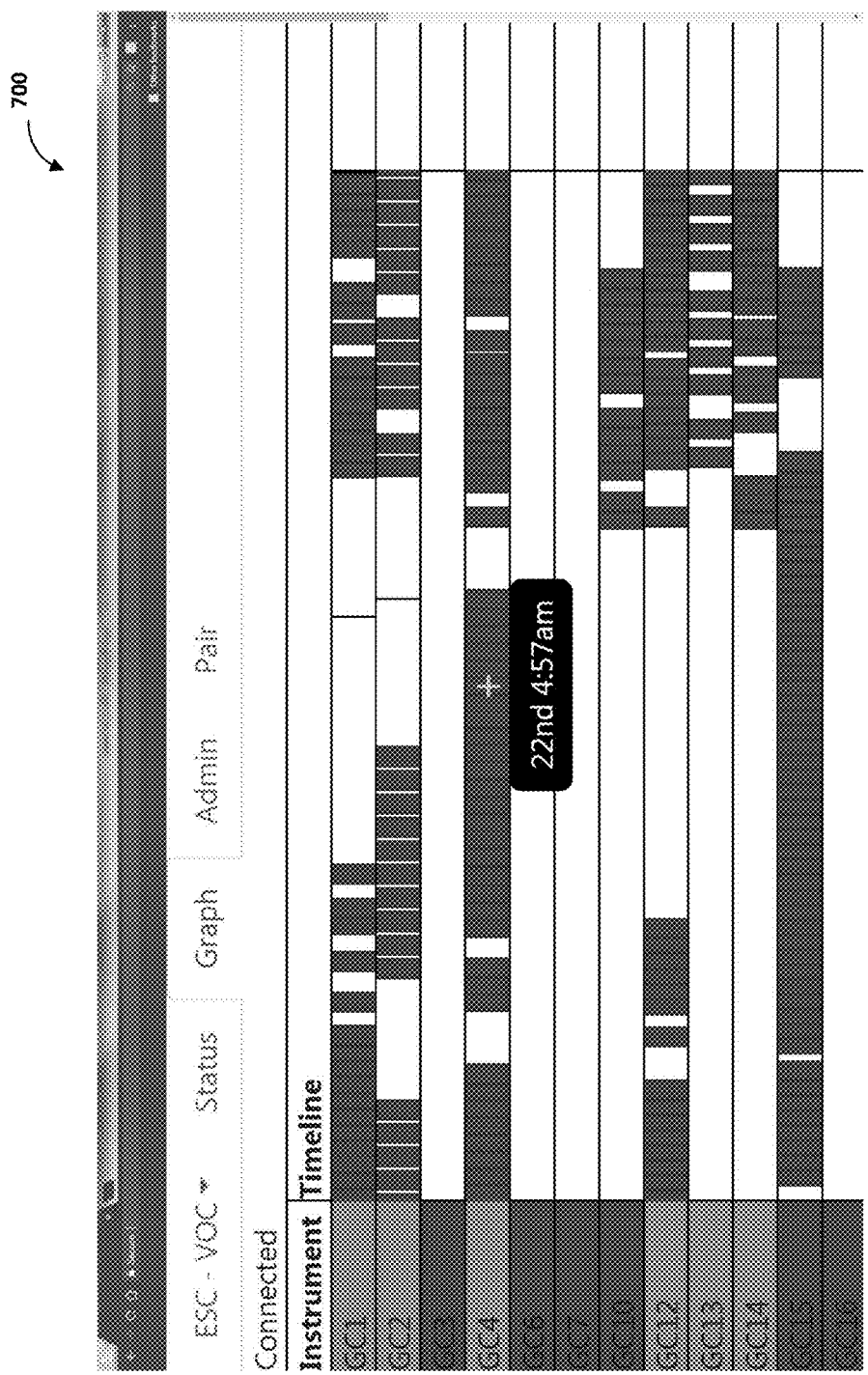
FIG. 7 is an illustration of a web page for displaying the status of chemical instruments connected to alarm modules, according to an example embodiment.

FIG. 7 is an illustration of a web page 700 for displaying the status of chemical instruments connected to alarm modules 320, according to an example embodiment. In an embodiment, the web page displays every chemical instrument that is monitored by a respective alarm module 320, and a timeline for every chemical instrument. For each chemical instrument, the timeline displays time periods when the respective chemical instrument was operating properly (in which case the time period is color-shaded, e.g., green) or not operating properly (in which case the time period is shown differently, such as leaving the space white). Symbols other than or in addition to color-shading may be used indicate proper or improper operation over a time period.

The name of each monitored chemical instrument is listed on the left-hand side, and each name is colored according to the status of the chemical instrument. For example, in FIG. 7, the label for "GC1" (gas chromatograph 1) is color-shaded, indicating that GC1 is currently operating properly. On the other hand, the label for "GC3" is color-shaded differently (e.g., red), indicating that GC3 is not operating properly. In an embodiment, the status of a chemical instrument is simply the operating status of the most recent time period for the respective chemical instrument. For example, if "operating properly" is the operating status of the most recent time period for a chemical instrument, then the label with the chemical instrument's name will be color-shaded in a first manner (e.g., color-shaded green or a particular darkness of gray). On the other hand, if "NOT operating properly" is the operating status of the most recent time period for a chemical instrument, then the label with the chemical instrument's name will be color-shaded in a second manner (e.g., color-shaded red or a different darkness of gray). Additional color-shadings may show different types of statuses. A distinct color-shading may indicate that connection to a server (link 325 in FIG. 3) is down. Another distinct color-shading may be used to indicate that one of the chemical processors ready for calibration or maintenance.

Figure 8:
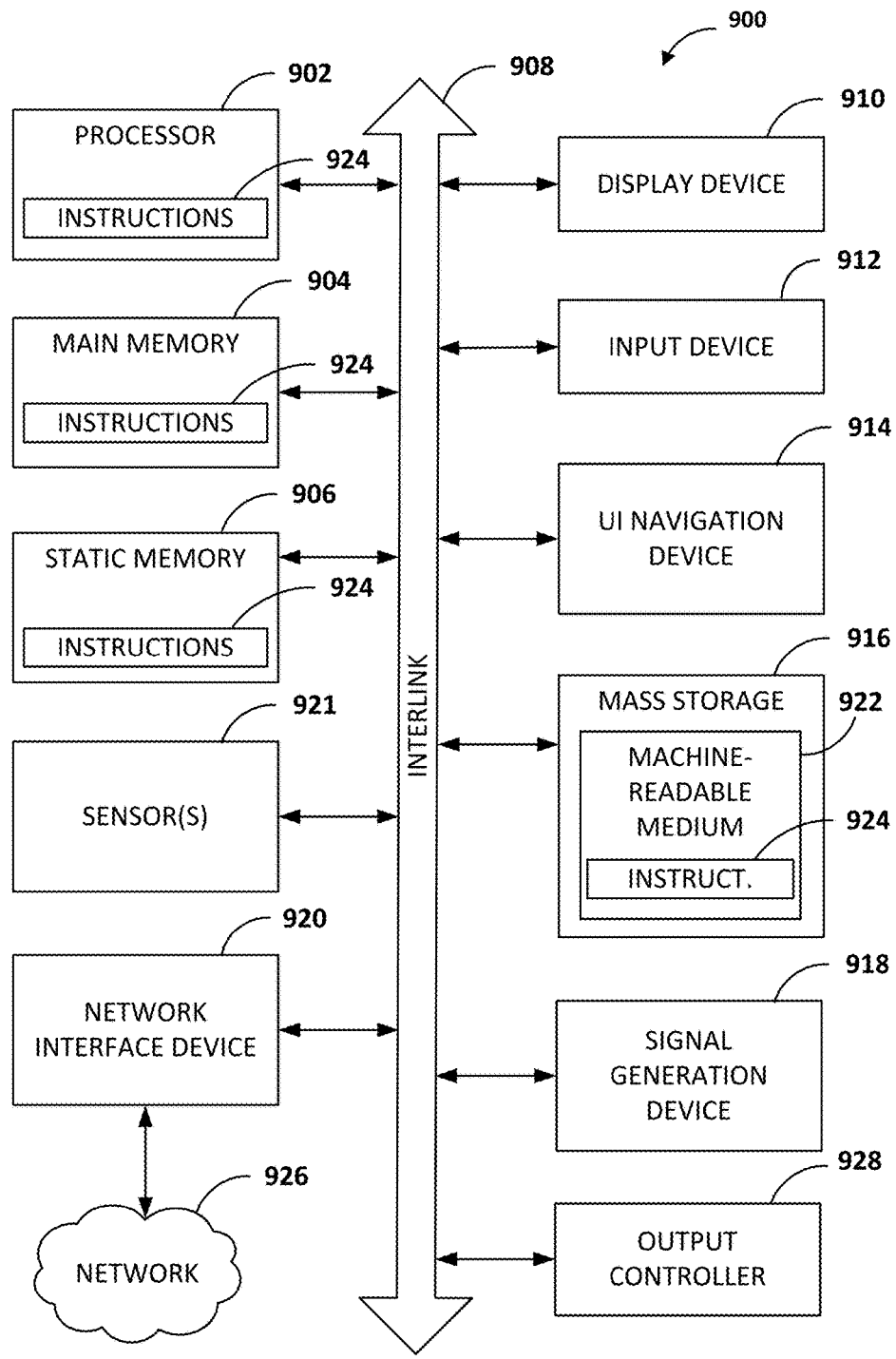
FIG. 8 is a block diagram illustrating an example of a machine, upon which any one or more example embodiments may be implemented.

FIG. 8 is a block diagram illustrating an example of a machine 800, upon which any one or more example embodiments may be implemented. In alternative embodiments, the machine 800 may operate as a standalone device or may be connected (e.g., networked) to other machines. In a networked deployment, the machine 800 may operate in the capacity of a server machine, a client machine, or both in a client-server network environment. In an example, the machine 800 may act as a peer machine in a peer-to-peer (P2P) (or other distributed) network environment. The machine 800 may implement or include any portion of the systems, devices, or methods illustrated in FIGS. 1-7, and may be a computer, a server, or any machine capable of executing instructions (sequential or otherwise) that specify actions to be taken by that machine. Further, although only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations, etc.

Examples, as described herein, may include, or may operate by, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810, an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., USB, parallel, or other wired or wireless (e.g., infrared (IR), near field communication (NFC), etc.) connection to communicate or control one or more peripheral devices (e.g., a printer, card reader, etc.)

The storage device 816 may include a machine-readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine-readable media.

Although the machine-readable medium 822 is illustrated as a single medium, the term "machine-readable medium" may include a single medium or multiple media (e.g., a centralized or distributed database, and/or associated caches and servers) configured to store the one or more instructions 824.

The term "machine-readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. Accordingly, machine-readable media are not transitory propagating signals. Specific examples of machine-readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); Solid State Drives (SSD); and CD-ROM and DVD-ROM disks.

The instructions 824 may further be transmitted or received over a communications network 826 using a transmission medium via the network interface device 820 utilizing any one of a number of transfer protocols (e.g., frame relay, Internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMAX®), IEEE 802.15.4 family of standards, Bluetooth®, Bluetooth® low energy technology, ZigBee®, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Conventional terms in the fields of computer systems and computer networking have been used herein. The terms are known in the art and are provided only as a non-limiting example for convenience purposes. Accordingly, the interpretation of the corresponding terms in the claims, unless stated otherwise, is not limited to any particular definition.

Although specific embodiments have been illustrated and described herein, it will be appreciated by those of ordinary skill in the art that any arrangement that is calculated to achieve the same purpose may be substituted for the specific embodiments shown. Many adaptations will be apparent to those of ordinary skill in the art. Accordingly, this application is intended to cover any adaptations or variations.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. Moreover, in the following claims, the terms "first," "second," and "third," etc. are used merely as labels, and are not intended to impose numerical requirements on their objects. In this document, a sensor set may include one or more sensors, which may be of different types. Furthermore, two different sensor sets may include one or more sensors that belong to both sensor sets.

In this Detailed Description, various features may have been grouped together to streamline the disclosure. This should not be interpreted as intending that an unclaimed disclosed feature is essential to any claim. Rather, inventive subject matter may lie in less than all features of a particular disclosed embodiment.

The above description is intended to be illustrative, and not restrictive. For example, the above-described examples (or one or more aspects thereof) may be used in combination with each other. Other embodiments may be used, such as by one of ordinary skill in the art upon reviewing the above description.

The invention claimed is:

1. An instrumentation alerting system for monitoring a readiness of a second chemical processor to receive a physical transfer of a chemical analyte from a first chemical processor, the instrumentation alerting system comprising:
   a timer configured to count time elapsed since receiving a transfer-ready signal;
   an alarm configured to trigger when the elapsed time counted by the timer exceeds a specified threshold, whereby the alarm trigger indicates that at least one of the first chemical processor and the second chemical processor is not operating properly; and
   a circuit, when connected to a communication link between the first chemical processor and the second chemical processor, configured to:
   monitor for the transfer-ready signal from the first chemical processor, wherein the transfer-ready signal indicates that:
   i) the first chemical processor received a receive-ready signal from the second chemical processor over the communication link;
   ii) the first chemical processor has completed processing the chemical analyte; and
   iii) the first chemical processor is ready to physically transfer the chemical analyte to the second chemical processor; and
   restart the timer based on receipt of the transfer-ready signal from the first chemical processor.

2. The instrumentation alerting system of claim 1, wherein the alarm is configured to cause a fault entry to be logged into a database when the elapsed time counted by the timer exceeds a specified threshold.

3. The instrumentation alerting system of claim 1, wherein the alarm is configured to cause an alert to execute when the elapsed time counted by the timer exceeds a specified threshold.

4. The instrumentation alerting system of claim 3, wherein the alert is at least one of:
an audible alarm; and
a visual alarm.

5. The instrumentation alerting system of claim 1, wherein the alarm is configured to cause a notification to execute when the elapsed time counted by the timer exceeds a specified threshold.

6. The instrumentation alerting system of claim 5, wherein the notification is at least one of:
transmission of an email to a specified email address;
transmission of a text message to an address of a device capable of receiving text messages, and
transmission of a telephonic call to a specified telephone number.

7. The instrumentation alerting system of claim 1, wherein the physical sample is a vial of liquid.

8. The instrumentation alerting system of claim 1, wherein the physical sample is a mixture of a gas with a carrier gas.

9. The instrumentation alerting system of claim 2, wherein the specified time period is between 5 and 45 minutes.

10. The instrumentation alerting system of claim 3, wherein the specified time period is thirty minutes.

11. The instrumentation alerting system of claim 1, wherein the transfer-ready signal further indicates that:
i) a third chemical processor has completed processing the chemical analyte; and
ii) the third chemical processor has physically transferred the chemical analyte to the first chemical processor.

12. The instrumentation alerting system of claim 1,
wherein the first chemical processor and the second chemical processor are configured to perform a continuous, sequential process whereby the first chemical processor processes chemical analytes and transfers the processed chemical analytes to the second chemical processor; and
wherein the second chemical processor does not send the receive-ready signal to the first chemical processor until the second chemical processor has completed processing one of the chemical analytes most recently received from the first chemical processor.

13. A method of monitoring a readiness of a second chemical processor to receive a chemical analyte from a first chemical processor, the method comprising:
starting a timer that counts time elapsed since receiving a transfer-ready signal;
monitoring for the transfer-ready signal from the first chemical processor, the transfer-ready signal indicating that:
i) the first chemical processor received a receive-ready signal from the second chemical processor;
ii) the first chemical processor has completed processing the chemical analyte, and
iii) the first chemical processor is ready to transfer the chemical analyte to the second chemical processor;
restarting the timer after receiving the transfer-ready signal;
triggering an alarm if the elapsed time counted by the timer exceeds a specified threshold, whereby the alarm trigger indicates that at least one of the first chemical processor and the second chemical processor is not operating properly.

14. The method of claim 13, further comprising:
causing a fault entry to be logged into a database when the elapsed time counted by the timer exceeds a specified threshold.

15. The method of claim 13, further comprising:
causing an alert to execute when the elapsed time counted by the timer exceeds a specified threshold.

16. The method of claim 15, wherein the alert is at least one of:
an audible alarm; and
a visual alarm.

17. The method of claim 13, further comprising:
causing a notification to execute when the elapsed time counted by the timer exceeds a specified threshold.

18. The method of claim 13, wherein the notification is at least one of:
transmission of an email to a specified email address;
transmission of a text message to an address of a device capable of receiving text messages; and
transmission of a telephonic call to a specified telephone number.

19. The method of claim 13, wherein the physical sample is a vial of liquid.

20. The method of claim 13, wherein the physical sample is a mixture of a gas with a carrier gas.

21. The method of claim 14, wherein the specified time period is thirty minutes.

22. The method of claim 15, wherein the specified time period is thirty minutes.

23. The method of claim 13, wherein the transfer-ready signal further indicates:
i) that a third chemical processor has completed processing the chemical analyte; and
ii) that the third chemical processor has physically transferred the chemical analyte to the first chemical processor.

24. The method of claim 13,
wherein the first chemical processor and the second chemical processor perform a continuous, sequential process whereby the first chemical processor processes a chemical analytes and transfers the processed chemical analytes to the second chemical processor; and
wherein the second chemical processor does not send the receive-ready signal to the first chemical processor until the second chemical processor has completed processing one of the chemical analytes most recently received from the first chemical processor.

25. The method of claim 22, wherein the receive-ready signal indicates:
1) the second chemical processor has completed processing of the previously received chemical analyte; and
2) the second chemical processor has physically transferred the previously received chemical analyte to another device.

26. A method of monitoring a readiness of a third chemical processor to receive a chemical analyte from a second chemical processor, the method comprising:
processing a chemical analyte by a first chemical processor;
transferring, from the first chemical processor to the second chemical processor, the processed chemical analyte;

further processing the processed chemical analyte by the second chemical processor to produce a further processed chemical analyte;

starting a time that counts time elapsed since receiving a transfer-ready signal;

monitoring for the transfer-ready signal from the second chemical processor, the transfer-ready signal indicating:
  i) that the second chemical processor received a receive-ready signal from the third chemical processor;
  ii) that the second chemical processor has completed processing the chemical analyte, and
  iii) that the second chemical processor is ready to transfer the chemical analyte to the third chemical processor;

restarting the time after receiving the transfer-ready signal; and triggering an alarm if the elapsed time counted by the timer exceeds a specified threshold, whereby the alarm trigger indicates that at least one of the first chemical processor, the second chemical processor, and the third chemical processor are not operating properly.

* * * * *